United States Patent
Chambers et al.

(10) Patent No.: US 7,819,283 B2
(45) Date of Patent: Oct. 26, 2010

(54) STRIP EJECTION SYSTEM

(75) Inventors: Garry Chambers, Mount Waverley (AU); Alastair Hodges, Mount Waverley (AU); David Sayer, Mount Waverley (AU)

(73) Assignee: Universal Biosensors Pty Ltd, Rowville (AU)

( * ) Notice: Subject to any disclaimer, the term of this patent is extended or adjusted under 35 U.S.C. 154(b) by 441 days.

(21) Appl. No.: 10/589,850

(22) PCT Filed: Feb. 17, 2005

(86) PCT No.: PCT/IB2005/000403

§ 371 (c)(1),
(2), (4) Date: Aug. 17, 2006

(87) PCT Pub. No.: WO2005/080966

PCT Pub. Date: Sep. 1, 2005

(65) Prior Publication Data

US 2007/0170200 A1    Jul. 26, 2007

Related U.S. Application Data

(60) Provisional application No. 60/545,161, filed on Feb. 18, 2004.

(51) Int. Cl.
*G07F 11/22* (2006.01)
(52) U.S. Cl. .................. 221/272; 221/268; 324/713; 324/718; 204/403.01; 204/403.02
(58) Field of Classification Search ............... 221/42, 221/43; 206/39, 39.4; 324/713, 178, 715; 204/403.02, 403.04, 406
See application file for complete search history.

(56) References Cited

U.S. PATENT DOCUMENTS

| 922,272 | A | * | 5/1909 | Garrod | 206/39.4 |
|---|---|---|---|---|---|
| 933,663 | A | * | 9/1909 | Pollock | 221/41 |
| 1,734,644 | A | * | 11/1929 | Ostrander et al. | 221/232 |
| 2,288,979 | A | * | 7/1942 | Testi | 221/231 |
| 3,308,989 | A | * | 3/1967 | Alltop et al. | 221/232 |
| 3,994,593 | A | | 11/1976 | Kato et al. | |
| 5,447,690 | A | | 9/1995 | Sugaya | |
| 5,635,135 | A | | 6/1997 | Kimura | |

(Continued)

FOREIGN PATENT DOCUMENTS

EP    0885591    12/1998

(Continued)

OTHER PUBLICATIONS

Abstract of JP 62-075263 in English translation, 1 page.

(Continued)

*Primary Examiner*—Gene Crawford
*Assistant Examiner*—Timothy R Waggoner
(74) *Attorney, Agent, or Firm*—Davis Wright Tremaine LLP

(57) ABSTRACT

A strip ejection system for holding and ejecting a strip is provided. The system includes a body and a strip movement section. The strip moving section includes all elements of the system that are involved with moving the strip, including a pressing element for pressing against the strip to move the strip from a first position to a second position. The pressing element is the only element of the strip movement section that is movable relative to the body.

24 Claims, 4 Drawing Sheets

U.S. PATENT DOCUMENTS

| | | | |
|---|---|---|---|
| 5,686,047 A | | 11/1997 | Augstein |
| 6,082,581 A | * | 7/2000 | Anderson et al. ............ 221/232 |
| 6,155,456 A | * | 12/2000 | Archer ........................ 221/231 |
| 7,138,089 B2 | * | 11/2006 | Aitken et al. .............. 422/82.01 |
| 2003/0106900 A1 | | 6/2003 | Storz |
| 2003/0121932 A1 | * | 7/2003 | Wajda ........................ 221/259 |

FOREIGN PATENT DOCUMENTS

| | | |
|---|---|---|
| EP | 1321769 | 6/2003 |
| EP | 1484601 | 12/2004 |
| EP | 1494021 | 1/2005 |
| JP | 05-188058 | 7/1993 |
| JP | 08-086785 | 4/1996 |
| JP | 2001-033418 | 2/2001 |
| JP | 2001-337066 | 12/2001 |
| JP | 2003-114213 | 4/2003 |
| WO | WO 02/08753 A2 | 1/2002 |
| WO | WO 03/042691 A1 | 5/2003 |
| WO | WO 03/082091 | 10/2003 |
| WO | WO 03/085392 | 10/2003 |

OTHER PUBLICATIONS

International Search Report of PCT Application No. PCT/IB2005/000403 (mailed Jun. 2, 2005), as published in WO 2005/080966 A1, published Sep. 1, 2005, pp. 21-23.

European Patent Office (EPO), Supplementary European Search Report mailed in corresponding European Application No. 05708544.1 dated Jun. 11, 2010, received Jun. 21, 2010, 4 pages.

Japanese Patent Office (JPO), Notice of Reasons for Rejection mailed in corresponding Japanese Application No. 2006-553703 dated Jul. 2, 2010, received Jul. 14, 2010, 6 pages.

European Patent Office Communication pursuant to Article 94(3) EPC, mailed in corresponding European Application No. 05708544.1 dated Jul. 30, 2010, received Aug. 9, 2010, 6 pages.

* cited by examiner

STRIP EJECTION SYSTEM

BACKGROUND OF THE INVENTION

1. Field of the Invention

The present invention relates generally to strip ejection devices. More particularly, the invention relates to portable strip ejection systems for medical test applications.

2. Related Art

In devices where a disposable element is to be located in a non-disposable element and the disposable element is used and then disposed of, it is often desirable to minimize contact between an operator and the used disposable element. This is particularly so for devices where blood or other potentially infectious agents are present in or on the disposable element. An example of such a device is a strip and meter based testing device for medical use. In this type of device, a disposable strip or other shaped element is filled with a biological sample such as blood, either while located or prior to being located in a meter that reads the test result.

BRIEF SUMMARY OF THE INVENTION

The invention is a simple to implement and robust system for incorporation into a non-disposable element. The system allows the operator to transport the disposable element (either within or outside of the non-disposable element) without having to contact the disposable element. In the case of transporting the disposable element outside of the non-disposable element, the invention functions as an ejection mechanism. In the case of transporting the disposable element within the non-disposable element, the invention functions to transport the disposable element to its position for use from an internal or external storage position. One or both of these functions can be performed by the invention. The invention will be described with reference to a disposable strip and meter based sensor device but it is to be understood that it is applicable to any device where it is desirable to be able to eject a disposable element from a non-disposable element with no direct operator contact with the disposable element.

Ejection systems for disposable strips in strip and meter based sensor systems are known. The blood glucose monitor marketed by Bayer Diagnostics under the name Glucometer ESPRIT™ in Australia and Ascensia™ DEX®2 in the USA transports the used strips via the movement of a set of levers and springs activated by the user sliding a pad on the face of a meter. This mechanism transports the strip from a cassette in the meter to the test position then ejects the strip after use. This is a relatively complicated system requiring multiple moving parts and is thus subject to mechanical failure. It also pushes the strip from the end and therefore has to be designed so as not to interfere with the electrical connection pins to the strip. Devices according to the invention seek to overcome the deficiencies in these devices by providing a simple system that can have only a single moving part, that is robust and easy to implement, and can operate on a portion of the strip away from the area of any electrical connection pins. The invention will be described with reference to a substantially flat strip shaped disposable element that is inserted into a port in the meter, however it is equally applicable to disposable elements with other shapes and non-disposable devices with functions other than metering.

Particular embodiments of the invention provide a strip ejection system for holding and ejecting a strip. The system comprising a body and a strip movement section. The strip moving section comprises all elements of the system that are involved with moving the strip. The strip moving section comprises a pressing element for pressing against the strip to move the strip from a first position to a second position. The pressing element is the only element of the strip movement section that is movable relative to the body.

Other embodiments of the invention provide a device having a pressing element for ejecting a strip from a body by transporting the strip from a first position to a second position, wherein a frictional force between a surface of the pressing element and at least one surface of the strip against which the surface of the pressing element is pressed transports the strip from the first position to the second position.

Other embodiments, as well as the structure and function of preferred embodiments will become apparent from a consideration of the description, drawings, and examples.

BRIEF DESCRIPTION OF THE DRAWINGS

The foregoing and other features and advantages of the invention will be apparent from the following, more particular description of preferred embodiments of the invention, as illustrated in the accompanying drawings wherein like reference numbers generally indicate identical, functionally similar, and/or structurally similar elements.

DETAILED DESCRIPTION OF THE INVENTION

Figure 1:
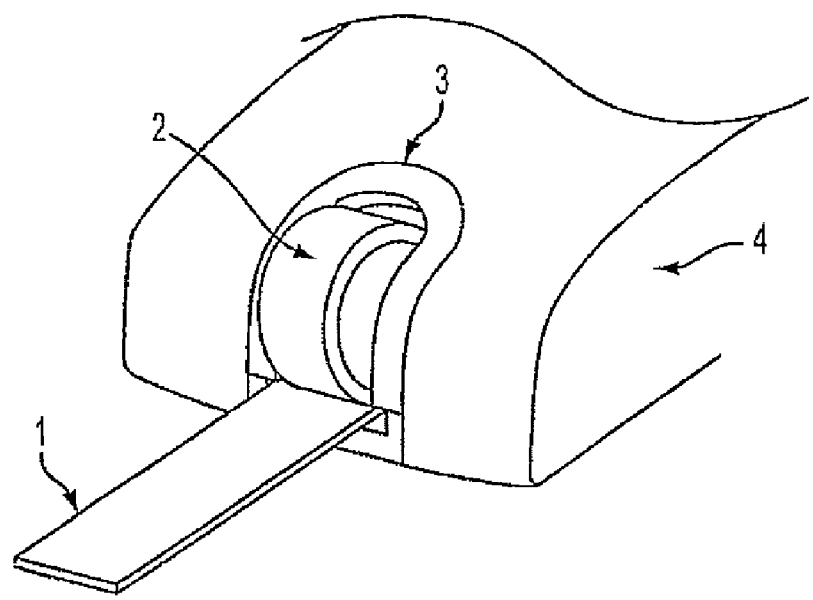
FIG. 1 shows a schematic illustration of a cylinder embodiment of the invention.

An exemplary embodiment of the invention is shown in the drawings and described herein.

The exemplary embodiment has a pressing element such as a cylinder, ball or plate that is pressed down against a face of the strip and moved to transport the strip into position in the meter port for a test to be performed, out of the meter port after a test has been performed, or both. In this disclosure, a strip face is taken to be an area of the strip that extends in a direction parallel to the direction in which the strip is to be transported. Examples of such areas are the large area faces of the strip that, with the strip laid flat would form the upper and lower faces of the strip or the smaller area faces that, with the strip laid flat would form the side edges of the strip. In operation, the pressing element is pressed against a face of the strip by the operator to make contact with the strip. The pressing element is then moved by the operator, while maintaining contact with the strip, such that the strip is transported into or out of the meter port by the operator movement. The pressing element is to be capable of a wide enough range of movement such that the strip can be transported to a position where it can be correctly located in the strip port to perform a test (in the case of transporting the strip to the meter port) or removed from the meter under gravity (in the case of moving the strip out of the strip port). After the strip is moved to such a position by the pressing element, the operator pressure on the pressing element is removed, either leaving the strip ready to perform a test (in the case of transport to the meter port) or freeing the strip and allowing it to fall away from the meter under the force of gravity (in the case of transporting the strip out of the meter port). In the latter case, the operator could be instructed, for example, to hold the meter and strip over a waste receptacle when ejecting the strip, such that when the strip falls it is received by the waste receptacle.

In an embodiment of the invention, the pressing element is a cylinder mounted on an axle that is located in the case of the meter. The cylinder is mounted such that it can be pressed down against a face of the strip and rotated relative to the meter case. The rotation can be achieved by allowing the cylinder to rotate relative to the axle, or more preferably by allowing the axle to rotate relative to the meter case. In a particular embodiment, the axle has sufficient movement within the holes or indentations in which the axle ends locate in the meter case to allow the cylinder to be pressed and moved down to contact the strip face. The strip can be transported by the operator pressing on the cylinder and rotating it so that the cylinder contacts the strip and simultaneously transports it in the direction of rotation. To be able to do this, when pressed against the face of the strip, the contact force between the cylinder and the face of the strip must be high enough relative to the forces holding the strip in the meter port to allow the strip to be moved by rotating the cylinder.

In a particular embodiment of the invention, the surface of the pressing element contacting the strip is be made of material with a suitable frictional coefficient such that the strip is moved by the pressing element when the latter is moved without requiring excessive pressing force. Examples of such material are polymers such as elastomers. Suitable elastomers include natural rubbers, synthetic rubbers, silicone rubbers and mixtures thereof. In a particular embodiment, the material is Thermoflex® (Plastic Technologies Service, Adelshofen, Germany).

This system has several advantages over known devices. It is simple. Essentially only one part is required to implement the device. It is robust to mechanical failure. There is no requirement for springs or fragile parts that could fail with repeated use and it is possible for all parts to be made by inexpensive plastic molding operations.

The applied force can be easily regulated by the operator. Unlike systems with springs and levers, the direct nature of this device allows the operator to easily feel and apply the correct pressing and rotating or sliding force to successfully transport the strip.

The invention is robust to transport failure. With more complicated mechanisms it is not always easy to reset and reapply the transport mechanism if it failed to work properly in the first instance. With the invention, however, it is a simple matter for the user to either carry on rotating the transport cylinder or remove the pressing force and slide back a pressing pad to re-contact the strip at a further point and ensure proper transport.

Since the invention can work by applying a pressing force to a face of the strip it is not necessary for the transport mechanism to act on the end edge of the strip located in the meter port. In strips where electrical connection between the meter and the strip is required, it is desirable to have the connection adjacent to the end of the strip inserted into the meter. This is desirable for cost reasons as it allows for a smaller area of strip to be located in the meter and therefore a smaller overall strip size to be used. It is also desirable for ergonomic and user recognition reasons where the user can clearly identify the connection area at the end of the strip in the case where the user inserts the strip into the meter.

Known transport systems act by pushing against the end edge of the strip. Since, for the reasons given above, the electrical connection pins are also often in this region, a design problem is presented where the connection pins and a transport pushing element need to be both fitted into a small area. In particular, the pushing element would be required to fit under or penetrate through the connection pin area, typically requiring small parts which could be fragile and difficult to handle in assembly during manufacture. A transport system according to the invention obviates this need by allowing the pressing element to be pressed against a flat face of the strip. This area of contact can be located away from the area of the electrical connection pins. It can be adjacent to or overlie the area occupied by the pins without interference or the necessity of using small parts. Thus is because it can be located on a face of the strip opposite to the face on which the electrical pins sit or, in the case of edge faces it can sit adjacent to the pins with an axis of movement perpendicular to the plane of the connector pins. It can also sit just in front of the pins on any face of the strip.

In another embodiment of the invention, a ball on an axle is used as the pressing element instead of a cylinder. This can have advantages in reducing the amount of space required by the device and also may allow the operator to more easily apply a greater pressure to the strip as the area of the wheel that contacts the strip will in most cases be smaller than for a cylinder of corresponding size. With a smaller contact area, a greater pressure can be applied by the same force.

In yet another embodiment of the invention, a sliding pad is used as the pressing element instead of a rotating cylinder or ball. In this embodiment, the operator applies pressure to the pad to contact the strip and then slide the pad in the direction that the strip is to be transported. To reset the mechanism, the pad can be retracted by the operator manually or the pad can be automatically retracted when a new strip is to be located in the meter port.

Embodiments of the invention are shown in FIGS. 1 to 6. In these Figures, the strip is shown in its test position, from which point it can be ejected. In the case of transporting the strip to the meter port, the pressing element is located to initially contact the strip near the end of the strip opposite to the electrical connection end. The pressing element is used to transport the strip such that the electrical connection end of the strip is aligned with the meter connection area at the end of the transport process. In this case, the strip may need to be presented to the transport mechanism from its storage position by a separate device.

The Figures will now be discussed in some detail. In FIG. 1, a substantially flat rectangular strip 1 is inserted into a port in meter casing 4. A cylinder 2 is positioned above strip 1 such that it can be pressed against an upper face of strip 1 by an operator. Further, cylinder 2 is mounted on an axle which extends into a collar 3, such that cylinder 2 can be rotated by a operator to eject strip 1 from the port.

Figure 2:
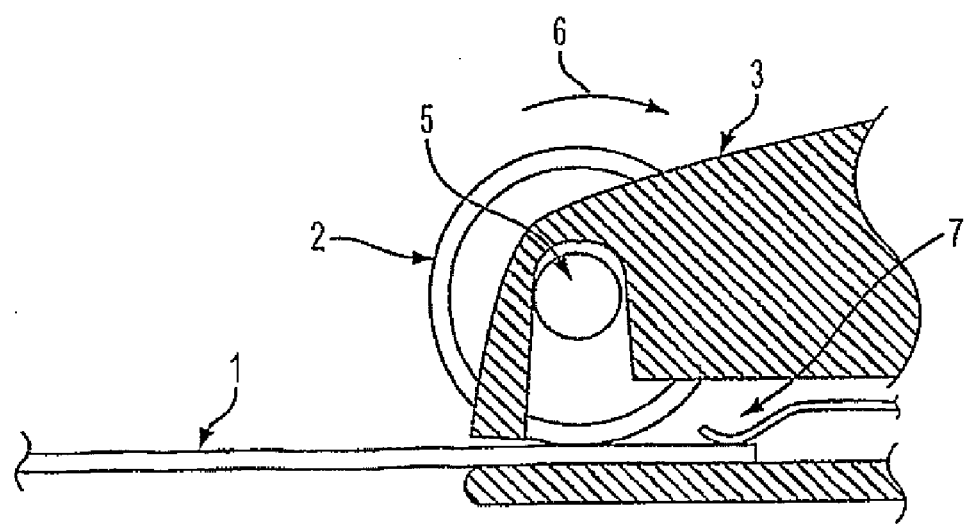
FIG. 2 shows a cross-section of the cylinder embodiment of the invention where the section is taken parallel to the ejection direction of the strip.

FIG. 2 shows a cross-section of the device shown in FIG. 1. The numbered elements in FIG. 2 correspond to the same numbered elements in FIG. 1. In addition, the axle 5 upon which cylinder 2 is mounted can be seen. The curved arrow labeled 6 shows the direction of rotation that would be imparted by an operator to eject strip 1 from the meter port. A connector pin 7 for the meter to make electrical connection to the strip is shown in a typical position.

Figure 3:
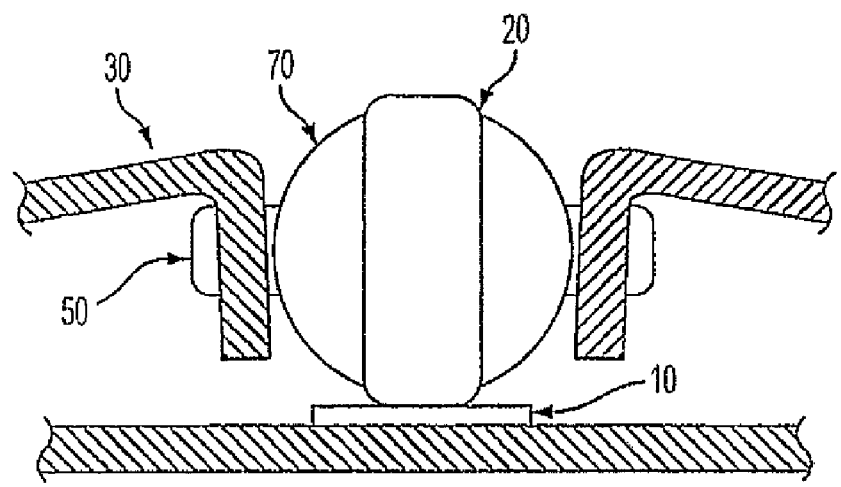
FIG. 3 shows a cross-section of a ball embodiment of the invention where the section is taken perpendicular to the ejection direction of the strip.

FIG. 3 shows an example of a cross-section of a ball embodiment of the invention viewed from the front. According to this embodiment, a raised section 20 of a ball 70 can be pressed against a disposable element 10 (or strip). The reduced area of contact between the pressing element (ball 70) and disposable element 10 compared to the cylinder embodiment means that a higher pressure can be applied by the operator for a given force.

Figure 4:
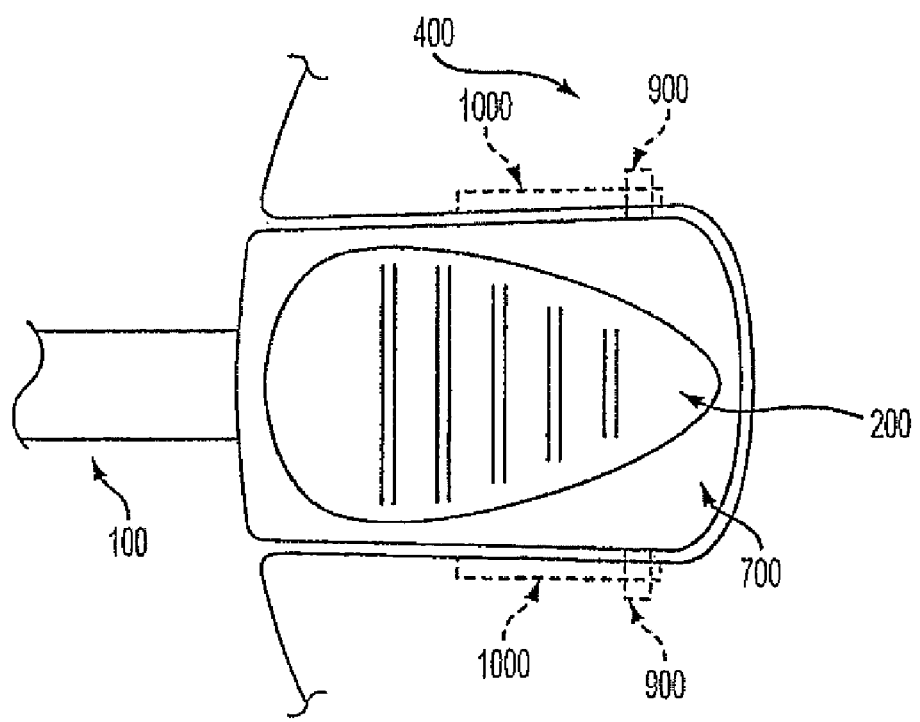
FIG. 4 is a top view of a plate embodiment of the invention.
Figure 5:
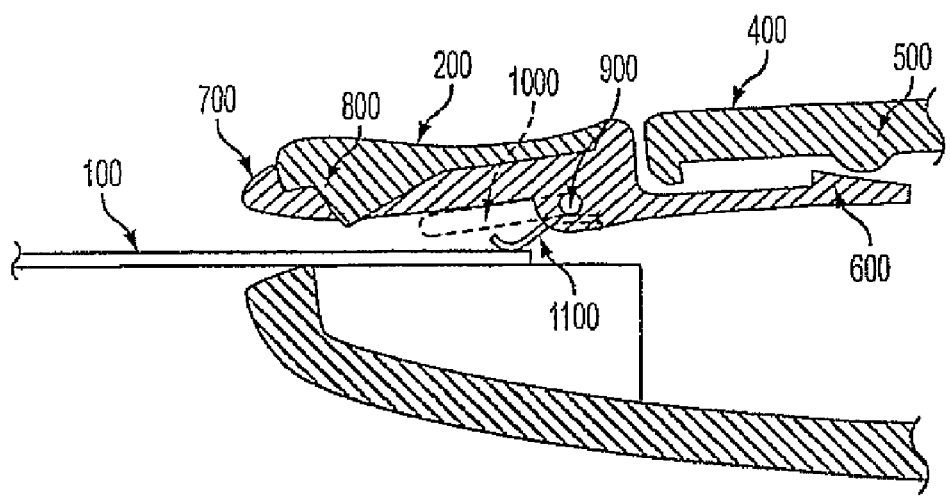
FIG. 5 is a cross-section of a plate embodiment of the invention where the section is taken parallel to the ejection direction of the strip and the plate is shown in its retracted position.
Figure 6:
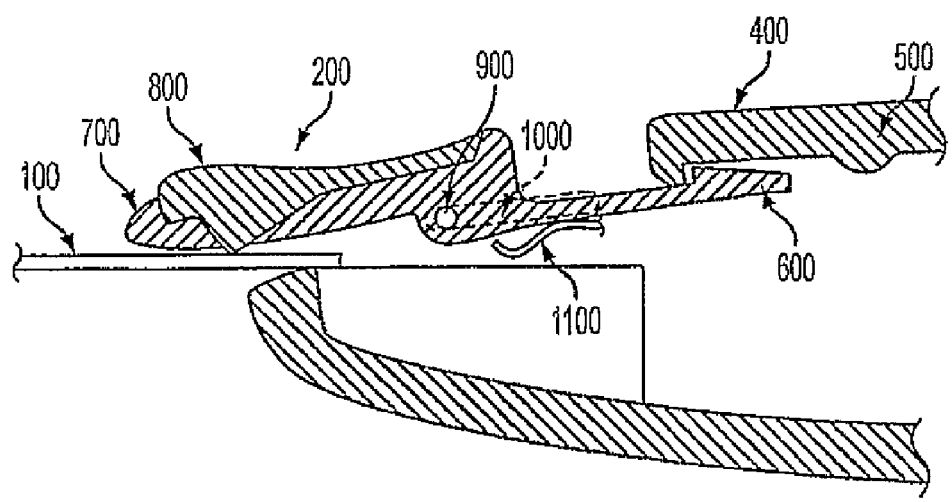
FIG. 6 is the same section as shown in FIG. 5 except with the plate shown in its extended pushing position.
Figure 7:
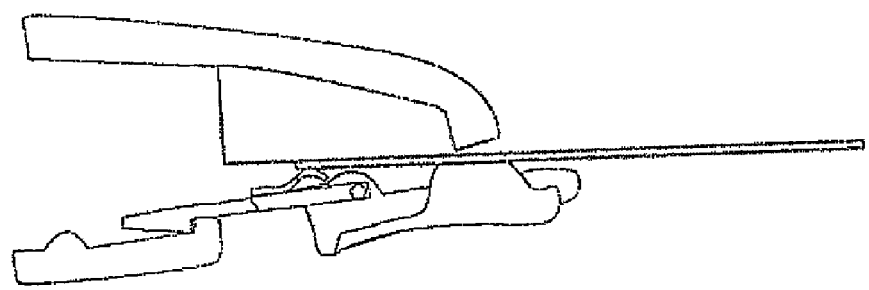
FIG. 7 depicts a plate embodiment of the invention where the pressing element presses against a lower face of the strip.
Figure 8:
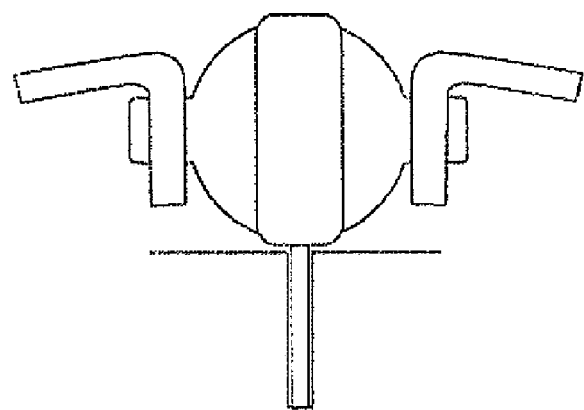
FIG. 8 depicts a ball embodiment of the invention where the pressing element presses against a side edge of the strip.

FIGS. 4, 5 and 6 show aspects of an example of a pad pressing element embodiment. In this embodiment, a pad 200 made of a soft material such as natural rubber is mounted in a plate body 700, which in turn is mounted to a case 400. The pad is shaped to have a protrusion 800 which can be brought into contact with a disposable element 100 in order to transport it out of the port to eject it. The plate body 700 has a barb 600 formed at, in this example, its innermost end. This barb has a dual purpose. It serves to retain plate body 700 to case 400 when plate body 700 is in its fully extended position, as shown in FIG. 6, and it acts against protrusion 500 to lift protrusion 800 away from disposable element 100 when plate body 700 is in its fully retracted position, as shown in FIG. 5. Plate body 700 is mounted to case 400 by pins 900 located in slots 1000, such that pins 900 can move along slots 1000 to advance and retract plate 700. An electrical connection pin 1100 is shown in a typical position in FIGS. 5 and 6.

In another embodiment of the invention the transport mechanisms disclosed are moved by a motorized assembly rather than by the operator directly. This has advantages in requiring less intervention by the operator but has increased complexity when compared to other embodiments.

What is claimed is:

1. A testing system comprising
a meter comprising a port for receiving a test strip; and
a strip transport assembly for transporting the strip into and/or out of the meter port, the strip transport assembly comprising:
 a body; and
 a strip movement section, the strip movement section comprising all elements of the assembly that are involved with moving the strip, the strip movement section comprising a pressing element for pressing against the strip to move the strip from a first position to a second position,
 wherein the pressing element is the only element of the strip movement section that is movable relative to the body, and
 wherein the body comprises an opposing surface opposite the strip movement section, wherein the opposing surface is immovable.

2. The system of claim 1, wherein the first position is a testing position in which the strip is used in a test.

3. The system of claim 2, wherein the second position is a disposal position in which the strip is removed from the system.

4. The system of claim 1, wherein the first position is a storage position in which the strip is stored, and
the second position is a testing position in which the strip is used in a test.

5. The system of claim 4, wherein the storage position is inside the body.

6. The system of claim 1, wherein the pressing element is a cylinder having protrusions along an axis of the cylinder.

7. The system of claim 6, further comprising receiving portions attached to the body, the receiving portions receiving the protrusions to define the movement of the cylinder.

8. The system of claim 7, wherein the receiving portions are open-ended slots.

9. The system of claim 1, wherein the pressing element is a ball having protrusions along an axis of the ball.

10. The system of claim 9, further comprising receiving portions attached to the body, the receiving portions receiving the protrusions to define the movement of the ball.

11. The system of claim 10, wherein the receiving portions are open-ended slots.

12. The system of claim 1, wherein the pressing element comprises a pad for receiving a user's finger or thumb.

13. The system of claim 12, wherein the pressing element further comprises at least one of a slot and a plurality of locating protrusions.

14. The system of claim 12, wherein the pressing element further comprises a plurality of locating protrusions and the body further comprises receiving portions that receive the locating protrusions.

15. The system of claim 14, wherein the receiving portions are slots.

16. The system of claim 13, wherein the pressing element further comprises a movement limiting portion that limits movement of the pressing element in a direction of strip movement from the first position to the second position.

17. The system of claim 13, wherein the pressing element is movable in a direction of strip movement from the first position to the second position, and in a direction substantially perpendicular to the direction of strip movement.

18. The system of claim 13, wherein pressing element further comprises an electrical connection pin for making electrical contact with the strip.

19. The system of claim 13, wherein the pressing element further comprises a strip contacting protrusion for contacting the strip.

20. The system of claim 1, wherein
the body further comprises slots,
the pressing element comprises
 a pad for receiving a user's finger or thumb;
 a plurality of locating protrusions that interact with the slots in the body; and
 a movement limiting portion that limits movement of the pressing element in a direction of strip movement from the first position to the second position, and
the pressing element is movable in a direction of strip movement from the first position to the second position, and in a direction substantially perpendicular to the direction of strip movement.

21. A testing system comprising
a meter comprising a port for receiving a test strip; and
a strip transport assembly for transporting the strip into and/or out of the meter port, the strip transport assembly comprising:
 a body; and
 a pressing element for transporting the strip from a first position to a second position of the body, wherein a frictional force between a surface of the pressing element and at least one surface of the strip against which the surface of the pressing element is pressed transports the strip from the first position to the second position, wherein the body comprises an opposing surface opposite the pressing element, wherein the opposing surface is immovable.

22. The system according to claim 21, wherein the surface of the strip against which the surface of the pressing element is pressed is an upper face of the strip.

23. The system according to claim 21, wherein the surface of the strip against which the surface of the pressing element is pressed is a lower face of the strip.

24. The system according to claim 21, wherein the surface of the strip against which the surface of the pressing element is pressed is a side edge of the strip.

* * * * *